United States Patent [19]

Ganguly et al.

[11] Patent Number: 4,890,624

[45] Date of Patent: Jan. 2, 1990

[54] FETAL HEART RATE COUNTING SYSTEM USING DIGITAL SIGNAL PROCESSING

[75] Inventors: Dipankar Ganguly, Redmond; Gary B. Sanders, Carnation, both of Wash.

[73] Assignee: Air-Shields, Inc., Hatboro, Pa.

[21] Appl. No.: 171,762

[22] Filed: Mar. 22, 1988

[51] Int. Cl.$^4$ .............................................. A61B 8/02
[52] U.S. Cl. .............................................. 128/661.07
[58] Field of Search .................... 128/661.07–661.1, 128/662.04

[56] References Cited

U.S. PATENT DOCUMENTS

| | | | |
|---|---|---|---|
| 3,934,577 | 1/1976 | Roman | 128/661.07 |
| 4,086,917 | 5/1978 | Burks et al. | 128/661.07 |
| 4,143,650 | 3/1979 | Hatke | 128/661.07 |
| 4,357,944 | 11/1982 | Manser et al. | 128/661.07 |

OTHER PUBLICATIONS

Courtin, E. et al., "A Versatile, Semi-Automatic Fetal Monitor", H P Journal vol. 28 No. 5 pp. 16–23, Jan. 1977.

Takenchi, Y. et al., "An Adaptive Correlation Ratemeter", Ultrasonics May 1978 vol. 16 No. 3.

Primary Examiner—Francis Jaworski
Attorney, Agent, or Firm—Ratner & Prestia

[57] ABSTRACT

A fetal heart rate counting system which includes a transducer element for transmitting an ultrasound signal into the fetal heart while the fetus is in utero and for receiving a returning Doppler signal frequency shifted by action of the fetal heart. The returning Doppler signal is processed to produce a forward heart movement Doppler signal, a reverse heart movement Doppler signal and the complete Doppler signal, from each of which fetal heart rate data is obtained. A composite fetal heart rate data is then produced from the three processed Doppler signal which is more accurate and complete than the data from any one signal individually.

25 Claims, 9 Drawing Sheets

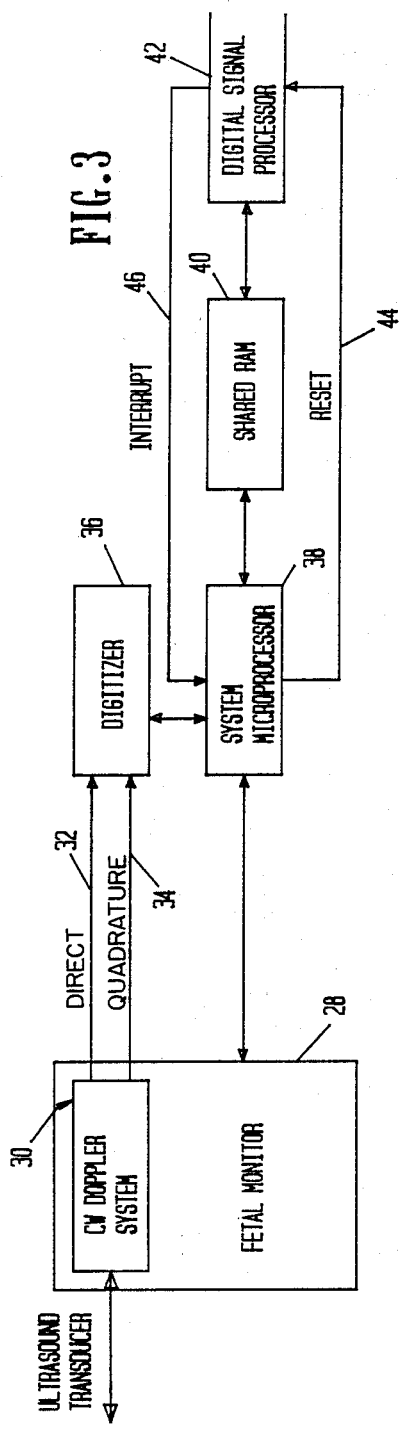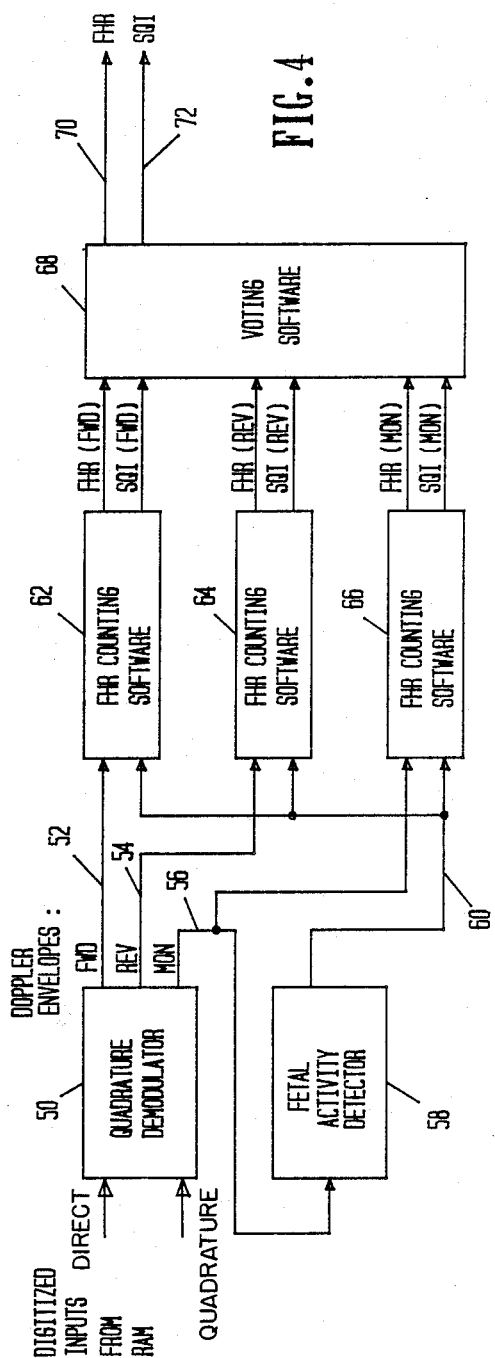

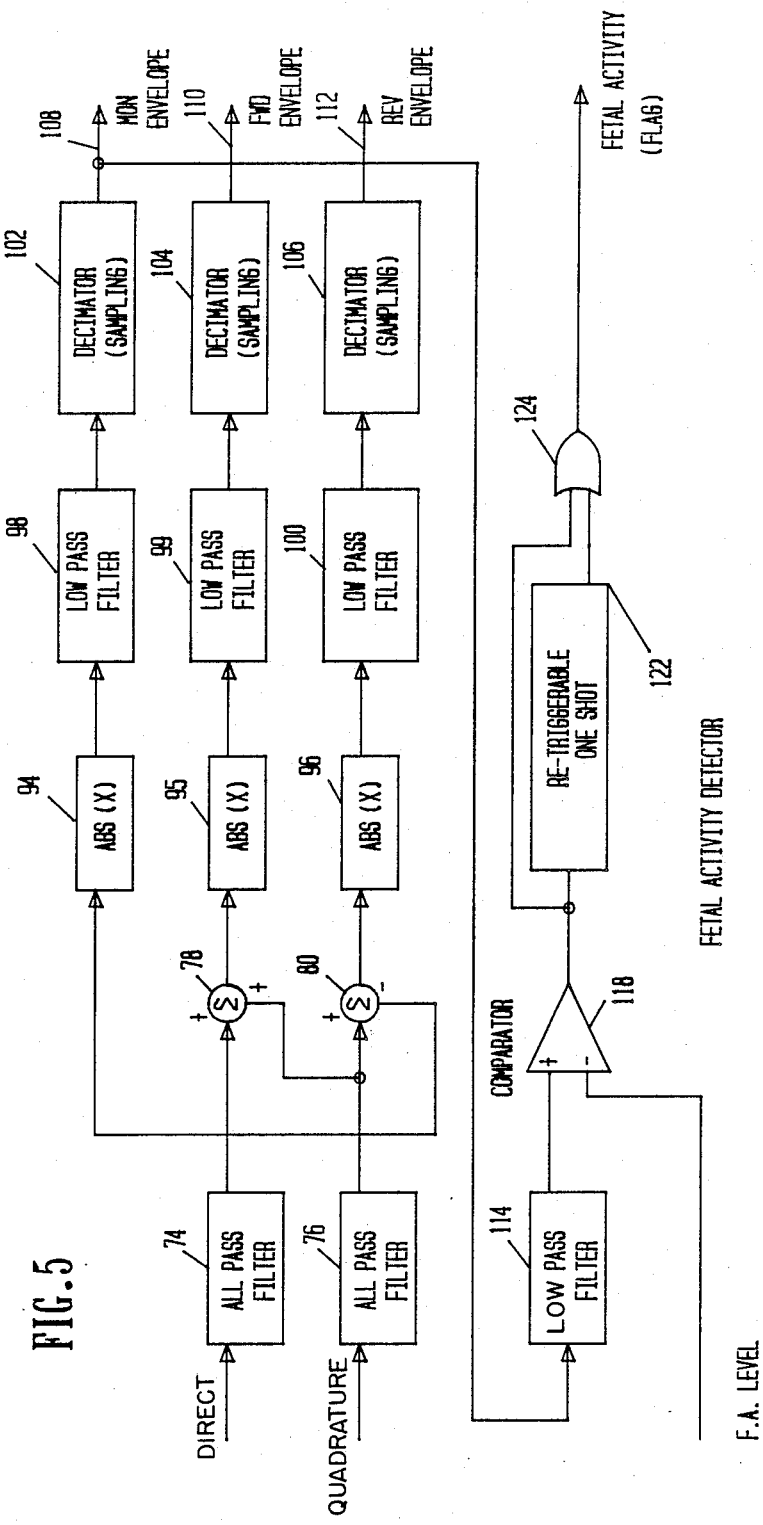

FETAL HEART RATE COUNTING SYSTEM USING DIGITAL SIGNAL PROCESSING

DESCRIPTION

1. Technical Field

This invention relates generally to the art of fetal heart rate counting using Doppler signal techniques, and more specifically concerns such a system in which an original returning Doppler signal is processed to produce a plurality of processed Doppler signals, each of which is representative of a component or aspect of the returning Doppler signal, wherein the plurality of processed Doppler signals are then further processed to select the most accurate fetal heart rate data among them at successive time intervals to produce a composite fetal heart rate record or trace.

2. Background Art

There is a significant need for accurate information concerning the fetal heart rate (FHR) in utero. It is desirable that such information be obtained non-invasively, i.e. without the nee for a probe which is inserted into the uterus of the mother. Most existing commercial fetal monitors which provide such non-invasive fetal heart rate information use conventional Doppler signal techniques to obtain the desired FHR information. However, it is known that such existing systems have certain disadvantages, including an action known as pen-lift, which may be due to several causes, in which the pen which records the fetal heart rate on a strip chart lifts off the paper. Pen-lift is quite undesirable, because during a pen-lift period, there is no information concerning the fetal heart rate provided by the monitor.

In addition, existing systems are susceptible, in varying degrees, to false data as well as double or half-counting errors, all of which are referred to as artifacts. Recognized false data is one of the significant causes of pen-lift.

Further, the signal processing techniques used to develop the FHR from the Doppler signals are often quite sophisticated and the resulting circuitry is typically difficult to repair or modify. Reliability of the heart rate counting portion of such systems has in the past also been a problem.

Disclosure of the Invention

Accordingly, the present invention includes a means for transmitting an ultrasound signal into the fetal heart while the fetus is in utero and means for receiving a returning Doppler signal from the fetus, frequency-shifted by action of the fetal heart, i.e. the movement of the fetal heart valve. The invention further includes means for processing the returning Doppler signal in such a manner to produce a plurality of processed Doppler signals, each such signal being characteristic of a different component of the returning Doppler signal and containing fetal heart rate data. Further, there is a means for then obtaining the fetal heart rate data from each of the processed Doppler signals and means selectively combining the fetal heart rate data from the processed Doppler signals in such a manner as to produce composite fetal heart rate data which is more accurate in total than the fetal heart rate data obtained from any one of the processed Doppler signals.

BRIEF DESCRIPTION OF THE DRAWINGS

FIG. 3 is a block diagram showing the hardware elements of a complete fetal heart rate counting system of, and including, the present invention.

FIG. 4 is a block diagram showing the software functions of the fetal heart rate counting system portion of FIG. 3.

FIG. 5 is a block diagram showing in more detail the functional implementation of the quadrature demodulator portion of the system shown in FIG. 4 and an implementation of a fetal activity detector used in conjunction therewith.

BEST MODE FOR CARRYING OUT THE INVENTION

The present invention is a part of a complete fetal heart rate (FHR) counting system. The counting system uses conventional Doppler signal techniques to obtain basic signal information from which fetal heart rate may be determined. The system includes a signal source which by means of a transducer external to the mother transmits an ultrasound signal having a relatively high frequency (1.875 MHz) to the fetus in utero. The transmitted ultrasound signal is reflected back to the external transducer by the action of the fetal heart valve. The movement of the fetal heart valve produces a slight shift in frequency of the returning signal due to the well-known Doppler effect. The returning ultrasound signal is converted to electrical signals by a transducer and applied to signal processing circuitry where the frequency shift is determined and an actual FHR count is obtained.

Conventionally, the implementation of the FHR signal processing is by means of a plurality of discrete hardware elements. In the embodiment described herein, the signal processing is implemented in software, although the drawings show the individual signal processing steps in block form, similar to that for discrete hardware elements. Sufficient information is provided herein to provide one familiar with computer software to produce an operable code to accomplish the required functions. However, the individual functions described could be implemented in hardware as well.

Figure 1:
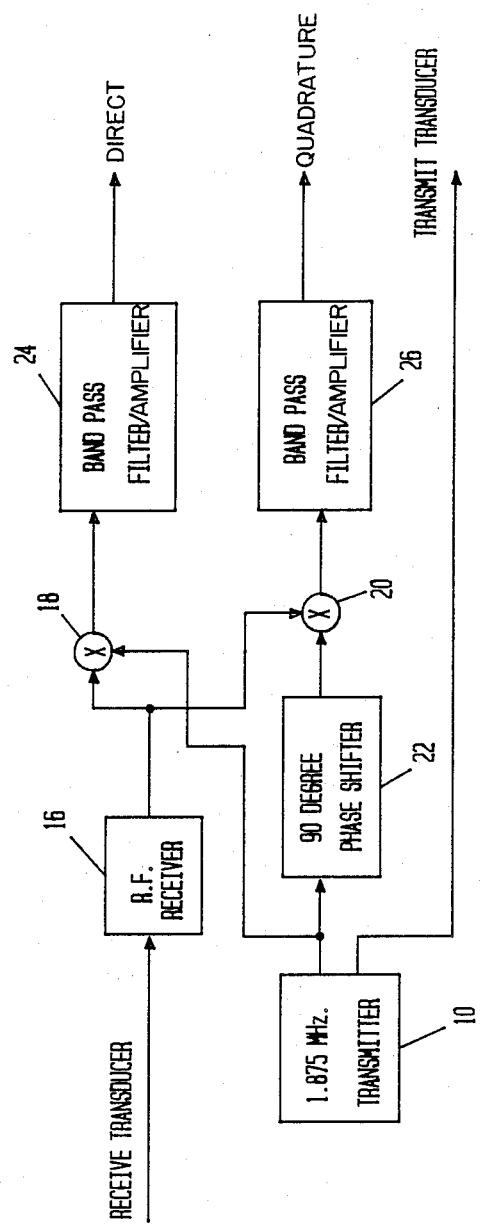
FIG. 1 is a block diagram of the general Doppler transmit/receive system associated with the present invention.

FIG. 1 shows the Doppler signal generation and receiver portion of the overall FHR counting system. It includes a signal generator/transmitter 10 which in the embodiment shown produces a 1.875 megahertz continuous wave (CW) transmit signal. This signal is applied to a transmit transducer which is positioned in use on the abdomen of the mother. The transmit transducer converts the CW signal into an ultrasound signal which is then transmitted through the uterus of the mother into the fetus. The ultrasound signal strikes the moving heart valve of the fetus and is reflected back, with a slight frequency shift, to a receiving transducer. It should be understood that the transmit and receive transducers may have a variety of configurations, and may include, for instance, a single transmitting element with multiple receiving elements arranged around the transmitting element, or more conventionally may include single transmitting and receiving elements.

Figure 2:
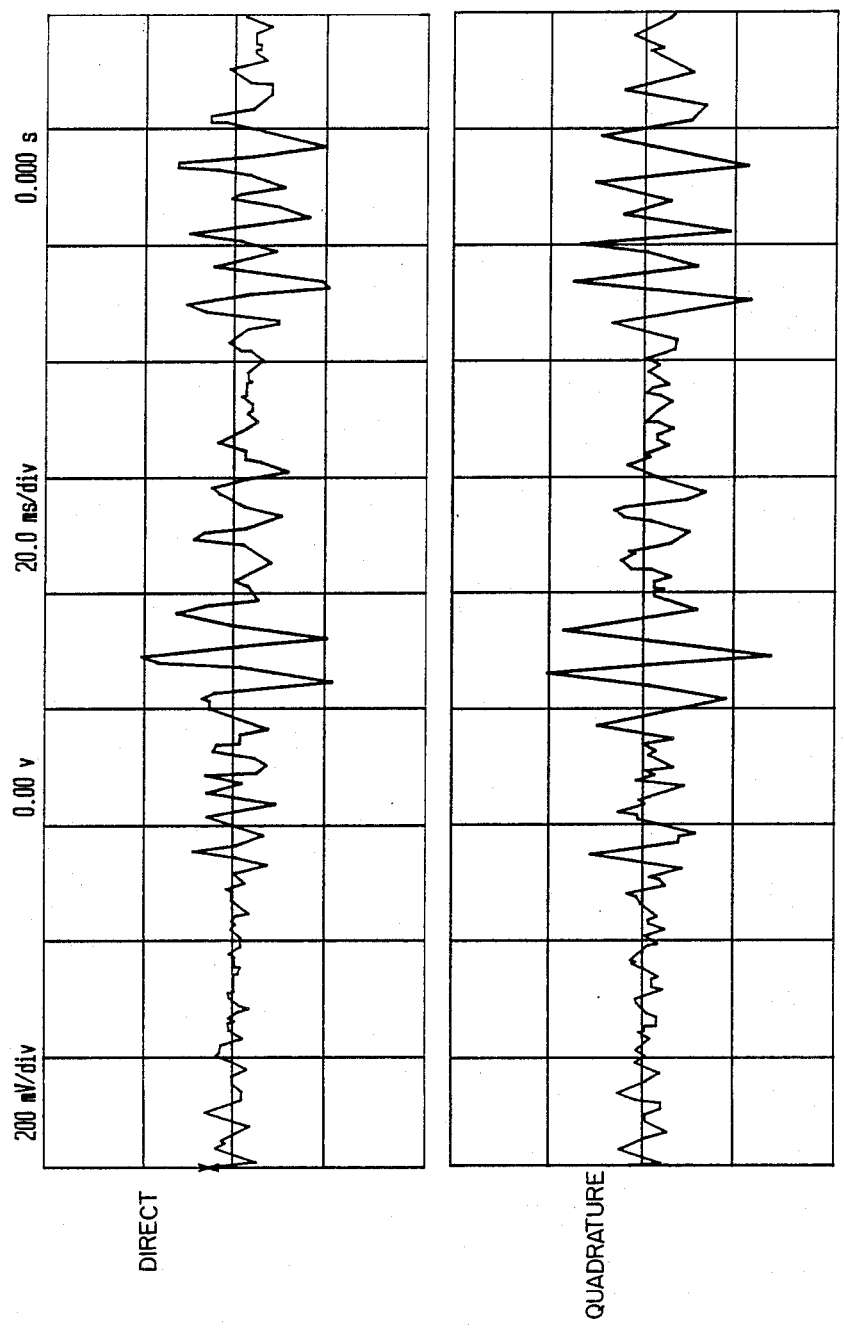
FIG. 2 is a signal diagram showing the audio output signal of the Doppler system of FIG. 1.

The electrical signals produced by the receive transducer are applied to and amplified by an RF receiver 16. The signal at the output of the RF receiver 16 is then applied to one port of each of two signal mixers 18 and 20. In mixer 18, the amplified signal from receiver 16 is mixed directly with the transmit signal from the signal generator/transmitter 10. In the other mixer 20, the amplified signal from receiver 16 is mixed with a 90V phase shifted version of the transmit signal, the phase shifting being accomplished by a conventional phase shifter 22. The output of mixers 18 and 20 are applied, respectively, to band pass filter/amplifier circuits 24 and 26. The output of circuits 24 and 26 are referred to, respectively, as the direct Doppler signal and the quadrature Doppler signal. FIG. 2 shows representative direct and quadrature Doppler signals.

FIG. 3 shows additional basic elements of the present invention for processing of the direct and quadrature Doppler signals produced by the circuit of FIG. 1. All of the elements/functions shown in FIG. 3 are actually part of a fetal monitor. Certain elements are shown specifically and the remainder of the fetal monitor is designated by the numeral 28. The Doppler signal transmission/receiving system for producing the direct and quadrature signals is shown generally at 30 and is referred to as the CW Doppler system. The ultrasound transducer transmits and receives the ultrasound signal to and from the fetus. The Doppler system produces the direct and quadrature Doppler signals on lines 32 and 34, as explained above. The direct and quadrature signals are then applied to a signed 12 bit digitizer 36 which samples the direct and quadrature signals continuously at a rate of 1.5 kilohertz.

The signals from the digitizer 36 are applied to a system microprocessor 38 which in the embodiment shown is an Intel 8088. In the embodiment shown, 15 samples of each Doppler signal, i.e. direct and quadrature, covering a total of 10 milliseconds, are collected by the microprocessor 38 and then written as a block of data into a random access memory (RAM) 40. Random access memory 40 is shared by system microprocessor 38 and a digital signal processor 42, which in the embodiment shown is a Texas Instrument TMS-32010. The RAM 40 is accessible by both the microprocessor 38 and the digital signal processor 42 on a non-simultaneous basis. Ordinarily, the digital signal processor 42 is held in reset by the system microprocessor 38 by virtue of a reset signal on line 44.

When a block (15 samples) of direct and quadrature Doppler signal data has been written into RAM 40, microprocessor 38 removes the reset from the digital signal processor 42, thereby giving the digital signal processor 42 control of RAM 40. When the digital signal processor 42 has control of RAM 40, it executes the instructions of the FHR counting software on the block of data in RAM 40, and when this is complete, it generates an interrupt signal over line 46 to the microprocessor 38. At this point, the results of the calculations performed by the processor 42 are present in RAM 40.

When the interrupt from the digital signal processor 42 occurs, the system microprocessor 38 again applies a reset signal on line 44 to the digital signal processor 42, which again gives the system microprocessor 39 control of RAM 40. Microprocessor 38 then reads the FHR results present in RAM 40 and transfers that information on line 41 to another portion of the fetal monitor 28 for display. Typically that display is in the form of a conventional strip chart. This process is repeated for each block of data (15 samples, 10 ms) sampled and collected in succession by microprocessor 38.

In the embodiment shown, the software includes microprocessor 38 control software which is typically a commercially available real-time executive program with the ability to interface to the selected hardware shown in FIG. 3 and to communicate with the other portions of the fetal monitor. The FHR counting software which is present in the digital signal processor 42 is responsible for generating the actual FHR count from the digitized Doppler signals (direct and quadrature) produced by the CW Doppler system on lines 32 and 34 (FIG. 3). As indicated above, the particular functions of the FHR counting software can, if desired, be implemented in hardware. The functions are shown as particular blocks in the drawings and will be the basis for further description of the invention.

The basic function diagram for the digital signal software is shown in FIG. 4. The digitized direct and quadrature Doppler signals in RAM 40 initially undergo a quadrature demodulation, as shown generally by block 50. Quadrature demodulation produces three Doppler envelope signals, referred to as forward, reverse and monitor, as will be explained further hereinafter. The forward, reverse and monitor signals on lines 52, 54 and 56, respectively, are each applied to, i.e. undergo, identical FHR counting software routines, 62, 64, 66 which count the FHR for each Doppler envelope signal. The monitor signal is also applied to a fetal activity detector routine or function 58, which produces an output signal on line 60 indicating the presence of a threshold level of fetal activity, as explained in more detail hereinafter.

The output of each FHR counting routine 62, 64, 66 produces a numerical FHR value plus a value referred to as a signal quality index (SQI), which is described in more detail hereinafter. These values are then applied to an FHR count select or voting routine 68, referred to as voting software, which selects what is determined to be the most accurate FHR count from among the three available for each block of sampled data in turn. The fetal heart rate count and the associated signal quality index (SQI) for that selected Doppler signal envelope are then produced as outputs on lines 70 and 72. As used hereinafter, the fetal heart rate count information produced by the FHR counting software is referred to as fetal heart rate data or FHR data. The output from the voting software, combining the fetal heart rate data from the three software routines 62, 64 and 66 is referred to as the fetal heart rate composite data. When the FHR data is displayed on a strip chart, it is referred to as a fetal heart rate trace or record.

FIGS. 5, 6, 7 and 8 show in more detail the FHR counting software of FIG. 4, as well as the signals at representative points throughout the processing of the Doppler signals. The signal processing system of the present invention, i.e. the TMS-32010, uses 16 bit signed fractional arithmetic, wherein the numbers are considered to all be greater than minus one but less than plus one. Eight bit integer calculations are used for other numerical operations, with the numbers being greater than zero but less than 255. Four index pointers are used in the embodiment shown and are described below. The letter identification for the pointers appear in the description of several functions/routines of the system.

i = index for data sampled at 1.5 KHz.
k = index for data deoimated by 100 Hz. sampling rate (10 ms).
n = index for data invoked by the fetal heart beat events.
j = index for data decimated by 2.5 Hz. sampling rate (400 ms).

Referring now to FIG. 5, the direct and quadrature Doppler signal groups or blocks (each group comprising 15 samples over 10 milliseconds) are first subject to all pass filtering shown at 74 and 76. In the embodiment shown, the all pass filters are infinite impulse response (IIR) filters, cascades of second order implementations of analog phase shifters, as discussed in *Digital Signal Processing* by Oppenheim and Schafer, Prentice-Hall, at pages 361-362, which in turn references similar filter work of S. D. Bedrosian. As used below, x(m) is the input to the filter and y(m) is the output.

$$y(m) = b0*x(m) + b1*x(m-1) + b2*x(m-2) + a1*y(m-1) + a2*y(m-2)$$

where:
m - sample index
b0,b1,b2,a1,a2 - constants
*indicates multiplication

ORDER : 4 (cascade of 2 second order sections)
BANDPASS : 50 Hz. to 500 Hz.
SAMPLE RATE : 1.5 KHz (index pointer $i$)
PHASE SHIFT : 90 +/− 0.5 degrees direct relative to quadrature in passband
COEFFICIENTS : (below)

Section 1, direct signal

| | | | | |
|---|---|---|---|---|
| b2 | = | +1 | a2 = | −0.074587 |
| b1 | = | +0.864376 | a1 = | −0.864406 |
| b0 | = | +0.074557 | | |

Section 2, direct signal

| | | | | |
|---|---|---|---|---|
| b2 | = | +0.499985 | a2 = | −0.319742 |
| b1 | = | −0.594379 | a1 = | +1.188696 |
| b0 | = | +0159856 | | |

Section 1, quadrature signal

| | | | | |
|---|---|---|---|---|
| b2 | = | +1 | a2 = | +0.069979 |
| b1 | = | +0.228095 | a1 = | −0.228126 |
| b0 | = | +0.070009 | | |

Section 2, quadrature signal

| | | | | |
|---|---|---|---|---|
| b2 | = | +0.499985 | a2 = | −0.565447 |
| b1 | = | −0.768242 | a1 = | +1.536424 |
| b0 | = | +0.282693 | | |

The output of the filter 74 is applied to one input of an adder 78, while the output of filter 76 is applied to one input of a subtractor 80. The output from filter 76 is applied to the other (add) input of adder 78 and thus is added to the output of filter 74, while the output of filter 74 is applied to the other (subtract) input of subtractor 80 and is thus subtracted from the output of filter 76. The adder and subtractor elements 78 and 80 implement the following transfer functions as significant steps in producing the forward and reverse Doppler signals referred to above:

Forward (FWD) (i) = 0.5* (Shifted direct signal (i))
+ 0.5* (Shifted quadrature signal (i))

Reverse REV (i) = 0.5* (Shifted direct signal(i))
− 0.5* (Shifted quadrature signal (i))

The outputs of filter 74, adder 78 and subtractor 80 each undergo full wave rectification [ABS(x) in FIG. 5] at 94, 95, 96, to produce Doppler envelopes. The Doppler envelopes are then low passed filtered at 98, 99 and 100. These filter implementations are also infinite impulse response filters, and are used to smooth out the Doppler envelopes to permit further sampling, i.e. resampling, of the signal. The specification for filters 98-100 are as follows:

ORDER 2 (1 second order section)
TYPE IIR Bilinear transform of Butterworth LPF
BANDPASS 20 Hz.
SAMPLE RATE 1.5 KHz. (index pointer $i$)
COEFFICIENTS (below)
Section 1

| | | | |
|---|---|---|---|
| b2 = +0.002503 | | a2 = | −0.863552 |
| b1 = +0.005505 | | a1 = | +1.853481 |
| b0 = +0.002503 | | | |

After low pass filtering, the envelopes undergo decimation, i.e. subsampling, at 102, 104, 106. Every 15th original sample is provided at the respective outputs. The i index pointer is associated with the input to the decimators while the k index pointer is associated with the output.

The decimated output on line 108 is a first Doppler envelope referred to as monitor (MON) and is the directly demodulated, filtered and decimated signal from the direct Doppler signal (FIG. 1). It represents the complete or total movement of the fetal heart valve. The output on line 110 is a second Doppler envelope referred to as forward (FWD), and represents the return Doppler signal produced by the forward movement of the fetal heart valve, i.e. the movement of the heart valve in a direction toward the external transducer, while the output on line 112 is a third Doppler envelope, referred to as reverse (REV), and represents the return Doppler signal produced by the reverse movement of the fetal heart valve, i.e. the movement of the heart valve in a direction away from the external transducer.

Still referring to FIG. 5, an implementation of a fetal activity detector is shown. The output on line 108, i.e. the Doppler MON envelope, is low pass filtered at filter 114, which separates the relatively low frequency fetal movement (body) from the fetal heart valve movement. The output from the low-pass filtering is applied at one input to a comparator routine 118. A threshold level signal indicating fetal activity is applied to the other input of comparator 118. In the embodiment shown, the fetal activity level is 0.062500.

When the signal from filter 114 is above the threshold level (0.062500), the resulting output from comparator 118 triggers a one shot multivibrator 122. The output of the one shot 122 is applied as one input to an OR gate 124. The other input to OR gate 124 is the output of comparator 118. There is an output signal from OR gate 124, indicating fetal activity, as long as one shot 122 has not timed out (2 seconds in the embodiment shown) or the fetal activity represented by the MON Doppler envelope is above the threshold level, as indicated by an output from comparator 118. In the embodiment shown, a software flag is set as long as an output from OR gate 124 exists.

Figure 6:
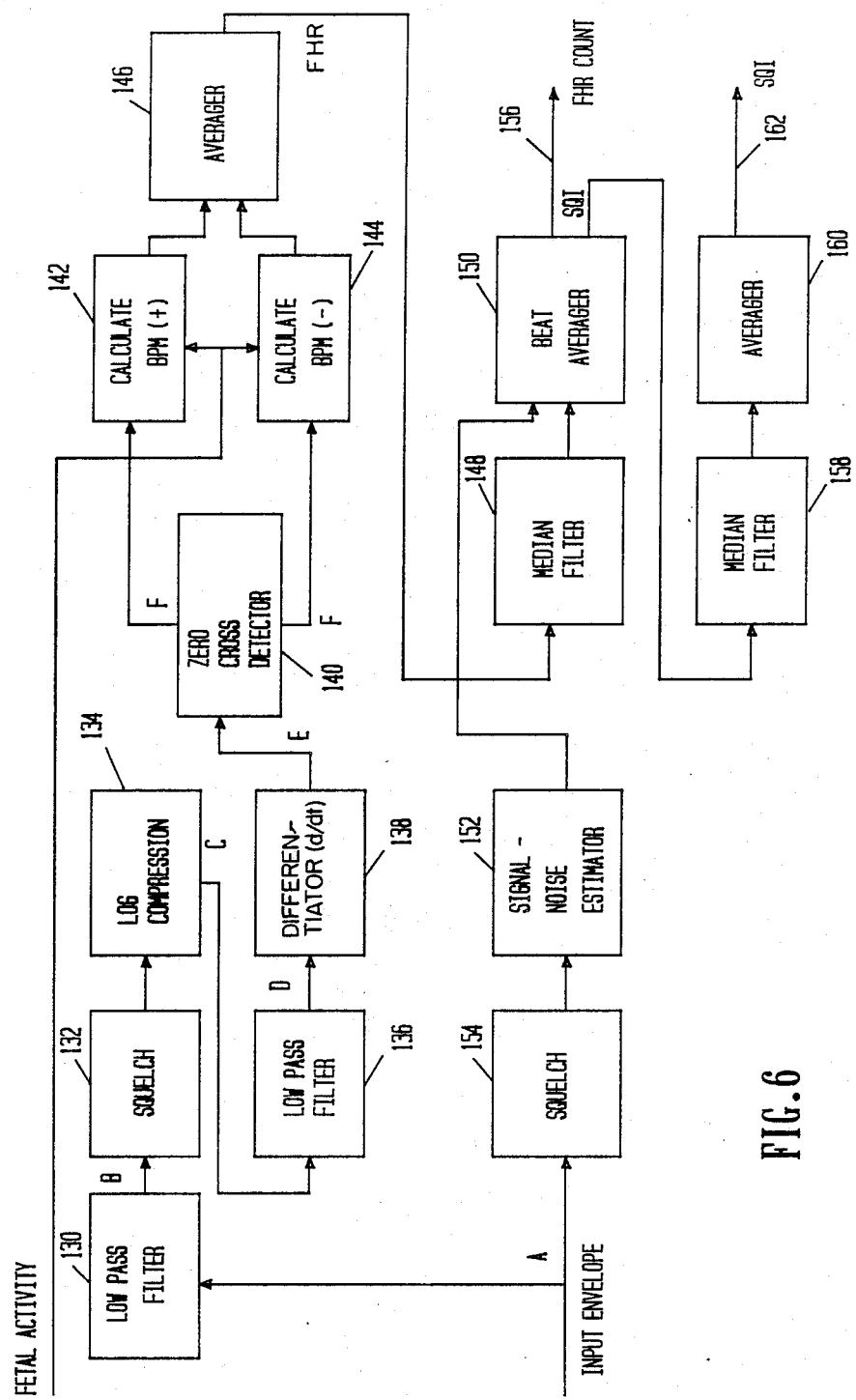
FIG. 6 is a block diagram showing the functional implementation of a portion of the FHR counting portion of the system of FIG. 4.

FIG. 6 is a block diagram of the software functions comprising the FHR counting software, shown as identical blocks 62, 64 and 66 in FIG. 4, operating on the FWD, REV and MON Doppler envelopes, respectively. The Doppler envelope signal output from the quadrature demodulator is low pass filtered at 130, which eliminates the high frequency signal components which are significantly above the typical values associated with fetal heart rate. The form of the transfer function (input/output) is the same as set out above for filters 74, 76. However, the specifications (coefficients) for the filter 130 are different, as set out below:

| | |
|---|---|
| ORDER | 4 (cascade of 2 second order sections) |
| TYPE | IIR Bilinear transform of Bessel LPF |
| BANDPASS | 2.5 Hz. |
| SAMPLE RATE | 100 Hz. (index pointer k) |
| COEFFICIENTS | (below) |
| Section 1 | |
| b2 = +0.011292 | a2 = −0.648000 |
| b1 = +0.022584 | a1 = +1.606494 |
| b0 = +0.011292 | |
| Section 2 | |
| b2 = +0.014893 | a2 = −0.731895 |
| b1 = +0.029817 | a1 = +1.677114 |
| b0 = +0.014893 | |

Figure 7:
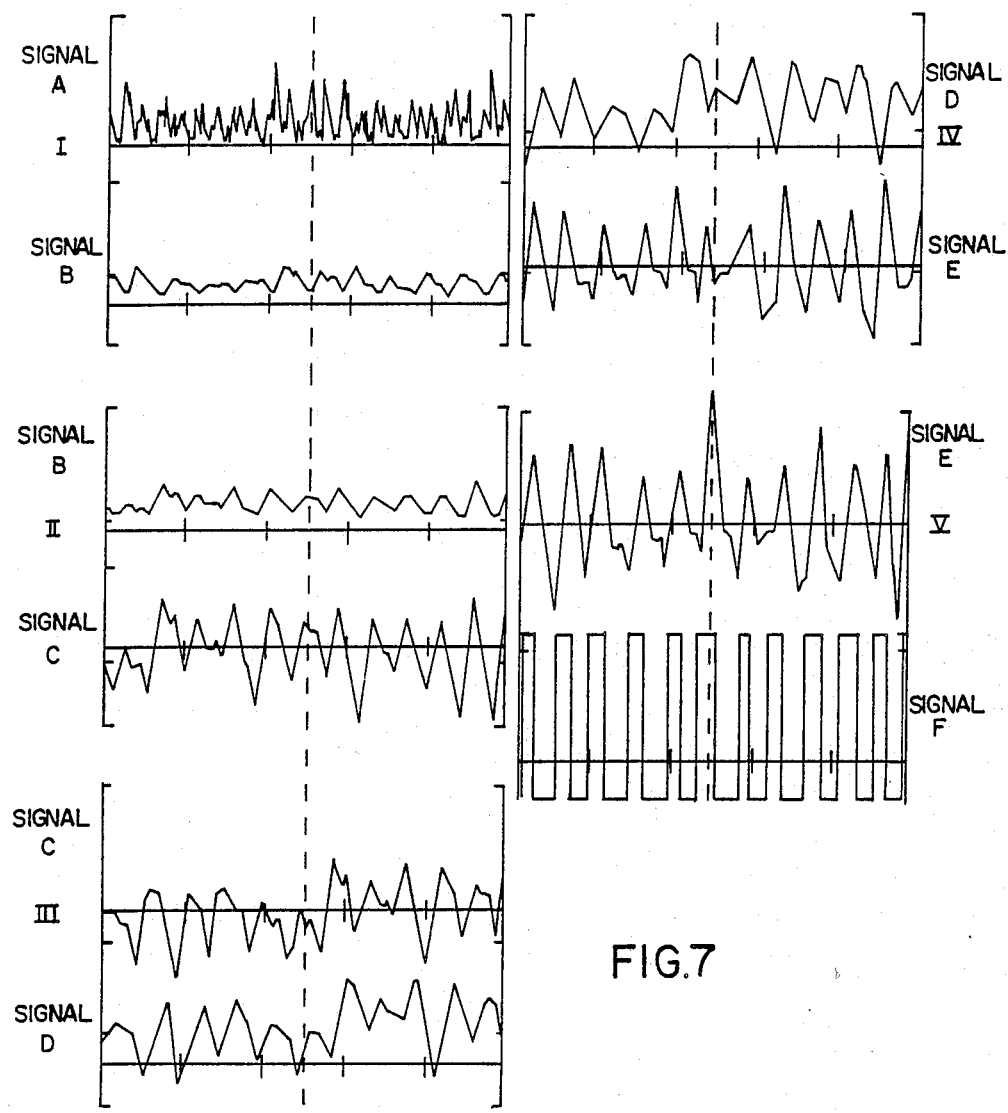
FIG. 7 shows a series of signal waveforms present at selected locations in the circuit of FIG. 4.

Typical examples of the signals present at points A and B in FIG. 6 are shown at A and B in FIG. 7 at part I. Following low pass filtering at 130, the resulting Doppler envelope undergoes a "squelch" function 132 to eliminate random noise and to limit signal input to the log compression routine 134 to positive numbers above a selected threshold. In the embodiment shown, the threshold is 0.00200. Values below this threshold are set to the threshold value.

The log compression routine 134 uses a Taylor's series approximation for the natural log function. As used below, y(k) refers to the input to the log compression routine and x(k) refers to the output. The transfer function of the log compression routine 134 is:

$$y(k) = 1 - c * \ln(x(k))$$

where: $c = 1 / \ln(\text{Threshold})$
$= -0.160911$
where: Threshold $< x(k) < 1$, then
$0 < y(k) < 1$ The signal envelope at the output of the log compression routine 134 is shown as signal C in FIGS. 6 and 7. The result of the log compression routine is to reduce or compress the dynamic range of the Doppler envelope such that the smaller amplitude fetal heart beat signals are normalized relative to the heart beat signals which are larger in amplitude. The log compression function also tends to minimize the effects of maternal respiration relative to variation in FHR amplitude.

The log compression routine, however, does produce an output signal having certain undesirable high frequency components, which are then filtered out through a low pass filter routine 136. Filter routine 146 is identical to low pass filter routine 130. The form of the signal output of the low pass filter 136 is shown as signal D in FIG. 7, part III.

The signal from the low pass filter 136 is then differentiated by routine 138, which produces a signal with zero crossings at the maximum values of the fetal heart rate waveform. This accomplishes the detection of the peaks of the fetal heart rate waveform. The transfer function for this routine appears below for the embodiment shown, where y(k) refers to the input and x(k) refers to the output.

$$y(k) = m * (x(k) - x(k-1))$$

where $m$ = gain constant
$= 16$ (for the embodiment shown)

The output of the differentiator routine 138 is shown as signal E in FIG. 6 and FIG. 7, part IV.

This waveform then undergoes zero crossing detection at 140, including event interpolation, as explained in more detail hereinafter, of the zero crossing to increase resolution, without additional sampling. Hysteresis is used to minimize spurious results from noise signals which cross zero at random intervals. The output, in the form of a digital square wave, is shown as F in FIG. 7, part V. The zero crossing detection routine is accomplished through the following transfer function, where x(k) refers to the input and y(k) the output, and the material in parenthesis is a comment on the function expressed.

$HTHR = HYSTR * y(k-1)$-(Calculate hysterisis threshold)

$y(k) = \text{sign}(HTHR - x(k))$- (Determine if $x(k)$ breaks the threshold)

$w(k) = \text{abs}(\{HTHR - x(k)\}/ \{x(k) - x(k-1)\})$-
(Event interpolation)

where:
HYSTR = hysterisis threshold
= −0.00200 (Same as squelch level)
$w(k)$ = event interpolation
$y(k)$ = +1 or −1 w(k) is a unitless quantity representing a fractional count of a sample interval between x(k−1) and x(k). Linear interpolation is used to estimate the actual point at which the waveform x(t) crosses the detection point at +HTHR for positive going signals and −HTHR for negative going signals.

The actual heart rate count is calculated from the output of the zero crossing detector routine, in blocks at 142 and 144. In routine 142, the leading edges of the output of the zero crossing detector 140 (signal F in FIG. 7) are counted and the FHR calculated in beats per minute. In 144, the trailing edges of the signal output from the zero crossing detector 140 are counted and FHR calculated in beats per minute. The average of the two FHR calculations is then calculated at 146.

In routine 146, the leading edges of the signals from the zero crossing detector are used as a master event for other parts of the system, and there is a flag set for those events as they occur. When such an event is detected, a counter m(k) is reset. The counter increments at selected time intervals if an event is not detected. The routine 146 further provides an interpolated FHR between subsequent events when an event does in fact occur, as follows:

$$FHR = kb/\{m(k) + w(n-1) - w(n)\}$$

where:
- $m(k)$ = counts between events (integer)
- $k$ = sample index
- $n$ = event index
- $kb$ = 6000
- = 60 sec./min * 100 counts/sec The k index, as indicated above refers to successive time intervals while the n index refers to fetal heart beat events. The w(n), w(n−1) etc. notations thus refers to w(k) discussed above, marked at particular times when a heart beat event has actually occurred. The routine is set to ignore spurious events which occur closer together in time than a 220 beat per minute (BPM) rate. A "pen-lift" signal (flag) is provided if no valid FHR activity is detected within a specified time, i.e. a 40 bpm interval in the embodiment shown or if a flag signal from the fetal activity detector is not present. The FHR rate is then rounded to an integer value between 40 and 220.

The output of averager 146, i.e. the fetal heart rate data, is then filtered by median filter routine 148. Median filtering removes spikes, i.e. anomalies, from the data without suppressing the actual signal or data trend information. The implementation in the embodiment shown is a 3 point recursive median filter initiated by the detection of a new fetal heart rate event. The implementation of the filter routine is shown below, where EVENT(n) is the incoming data input or event and MEDF(n) is the new median event.

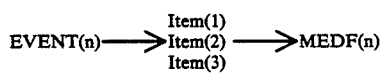

An ordered list is kept within the median filter routine such that Item(1)>Item(2)>Item(3). The incoming data EVENT (n) is inserted into the list in the following manner and the new Item(2) or the median point of the list is reported as MEDF(n)

| if | EVENT (n) > Item (1) | |
|---|---|---|
| then | Item (3)' = Item (2) | |
| | Item (2)' = Item (1) | MEDF (n) = Item (1) |
| | Item (1)' = EVENT (n) | |
| if | Item (2) < EVENT (n) < Item (1) | |
| then | Item (3)' = Item (2) | |
| | Item (2)' = EVENT (n) | MEDF (n) = EVENT (n) |
| | Item (1)' = Item (1) | |
| if | Item (3) < EVENT (n) < Item (2) | |
| then | Item (3)' = EVENT (n) | |
| | Item (2)' = Item (2) | MEDF(n) = Item (2) |
| | Item (1)' = Item (1) | |
| if | EVENT (n) < Item (2) | |
| then | Item (3)' = EVENT (n) | |
| | Item (2)' = Item (3) | MEDF (n) = Item (3) |
| | Item (1)' = Item (2) | |

The output of the median filter routine 148 is then applied as one input to a beat averager routine 150. The actual operation of averager 150 is described below. The other input to beat averager 150 comes from a signal to noise estimator routine 152 which in turn is responsive to the original input envelope shown as signal A in FIG. 6 which has been subsequently modified by a squelch routine 154, which is identical to squelch routine 132.

The signal to noise estimator calculates an approximation of signal quality with respect to noise by comparing the maximum signal value versus minimum signal value over the interval of a single fetal heart beat event. The operation of the signal to noise estimator routine 152 is initiated by each new fetal heartbeat event and provides an average indication of signal amplitude relative to noise. If the FHR signal waveform is noisy, then the maximum/minimum signal values for the signal envelope (MON, FWD or REV) will be close to each other in amplitude and the signal to noise estimator output will be close to zero. In the embodiment shown, a signal envelope with a large difference between maximum and minimum amplitudes will produce an output from routine 152 which is close to a particular value, 127 in the embodiment shown. The routine is outlined below, where DATA(k) refers to the input FHR data and the material in parenthesis are comments. If no new fetal heart beat event is detected,

| then | | |
|---|---|---|
| MAX(k) | = | MAXIMUM (DATA(k),MAX(k − 1)) - (Signal level estimate) |
| MIN(k) | = | MINIMUM (DATA(k),MIN(k − 1)) - (Noise level estimate) |
| SNR(n) | = | same (no change) |

This procedure will pick out the minimum and maximum data values over one heart beat cycle. If a new event is detected,

| then | | |
|---|---|---|
| SNR(n) | = | 127 * (MAX(k) − MIN(k) )/MAX(k) |
| MAX(k) | = | −1 |
| MIN(k) | = | +1 - (Re-initialize MAX(k) and Min(k)) |

The beat averager routine 150 determines the beat to beat variation in time of the FHR information from filter 148 and also processes the signal to noise estimator information. If the signal to noise estimate value is below a selected threshold, then the output on line 156 is a pen-lift. In the embodiment shown, the threshold value is 93. Also, if there is a large beat to beat variation of the incoming FHR, the value of which is selected empirically, a pen-lift results. If there is no pen-lift, the successive numerical values, following processing by an 8 point adaptive averager, on line 156 is the FHR count.

With respect to beat averager 150 in more detail, the input information is, as pointed out above, the output from median filter 148 in beats per minute i.e. BPM(n), and the output from routine 151, i.e. SNR(n). BEAT(n) refers to the output of averager 150. The details of the routine are summarized below. If no new fetal heart beat event is detected, then return.

If a new event is detected:

(a) Penlift for poor SNR(n):

If SNR(n) < SIGNZ, then set BPM'(n) = zero
otherwise set
BPM'(n) = BPM(n)
where
SIGNZ = Poor signal threshold
= 93 (integer, chosen empirically from clinical data)
BPM(n) = input FHR
BPM'(n) = intermediate value (b) Eight beat adaptive averager:

if $n \geq$ VBEATS $$BEAT(n) = (1/n) * \sum_{m=0}^{7} BPM'(n-m)$$

Pen-lift output for large number of penlifted incoming beats:

if n<VBEATS, BEAT(n)=0

Pen-lift output for large beat to beat variation of incoming beats:

DELTAB(n) = abs ( BPM'(n) − BPM'(n − 1) )
If DELTAB(n) > BDELTA then BEAT(N) = 0
where
N = # of new zero (penlift) events in the past history buffer of BPM'(n) thru BPM'(n − 7) including pen-lifts generated in the step (a)
VBEATS = Valid beat threshold
3 (chosen empirically)
BEAT(n) = input data processed in step (a)
BDELTA = variability threshold
= 3 (chosen empirically)

The beat to beat variation of the FHR is scaled to be greater than zero but less than 120. A numerical value referred to as signal quality index (SQI) is obtained by averaging the beat to beat variation with the signal-to-noise estimate value obtained from routine 152. SQI is thus a composite index number that takes into account both signal quality in terms of beat to beat variation of the fetal heart rate and the signal-to-noise ratio estimate of the Doppler envelope. The SQI index is an interger, in the embodiment shown, between zero and 123. In more detail the SQI index is determined as follows:

Scale beat to beat variation to an interger in the range 0 < DELTAB(n) < 120, with 120 representing 15 BPM of variation IF DELTAB(n) > 15 THEN DELTAB (n) = 15
DELTAB(n) = 8 * (15 − DELTAB(n) )

Calculate SQI(n) by averaging SQI(n) with SNR(n) ;
SQI(n) = {DELTAB(n) + SNR(n) } / 2

The SQI value from the beat averager 150 is then applied to a median filter routine 158 identical to that of median filter 148 and the results of that routine are applied to a 7 point adaptive averager 160 to smooth the signal trend of the SQI signal. The SQI output of averager 160 appears on line 162.

A summary of the implementation of the adaptive averager 160 appears below. INPUT(n) refers to the input to the averager while AVGR (n) refers to the output thereof.

If no new event is marked, then return.
If a new event is marked:

Adaptive averager:
if $n \geq$ VTMIN $$AVGR(n) = (1/n) * \sum_{m=0}^{P-1} INPUT(n-m)$$

Flag a pen-lift of the output for large number of pen-lifted incoming beats:

if n < VTMIN,  PLFLAG = 1
otherwise    PLFLAG = 0

Flag a pen-lift of the output for large beat to beat variation of incoming beats:

BTVAR1(n) = abs ( INPUT(n) − INPUT(n − 1) )
if      BTVAR1(n)>BTDELT then PLFLAG = 1 where:
n = # of non zero (pen-lift) events in the past history buffer of INPUT(n) thru INPUT(n − 7)
VTMIN = Valid beat threshold
= 3 (Chosen empirically)
AVGR(n) = output of averager
INPUT(n) = input data
BTDELT = variability threshold
= 3 (Chosen empirically)
P = length of the averager
= 5 or 7 depending on application A seven point adaptive order averager is used on SQI(n) in which the output is not penlifted when flagged by PLFLAG =1. SQI(n) is not penlifted in this embodiment to preserve continuous information pertaining to signal quality.

As seen from FIG. 4, the above described FHR counting software produces both fetal heart rate data, with or without periodic pen-lift indications, and an SQI index value, for each of the three Doppler signal envelopes produced by the quadrature demodulator 50, i.e. FWD, REV and MON described above. This total of six signals (FHR count and SQI index for each Doppler envelope) are then processed by FHR signal voting software shown in FIG. 8. The signals are applied to the voting routine element 162. The routine 162 is initiated (invoked) in the particular embodiment shown by the presence of a new FHR event in the MON mode, i.e. a signal on the MON FHR input line.

Figure 8:
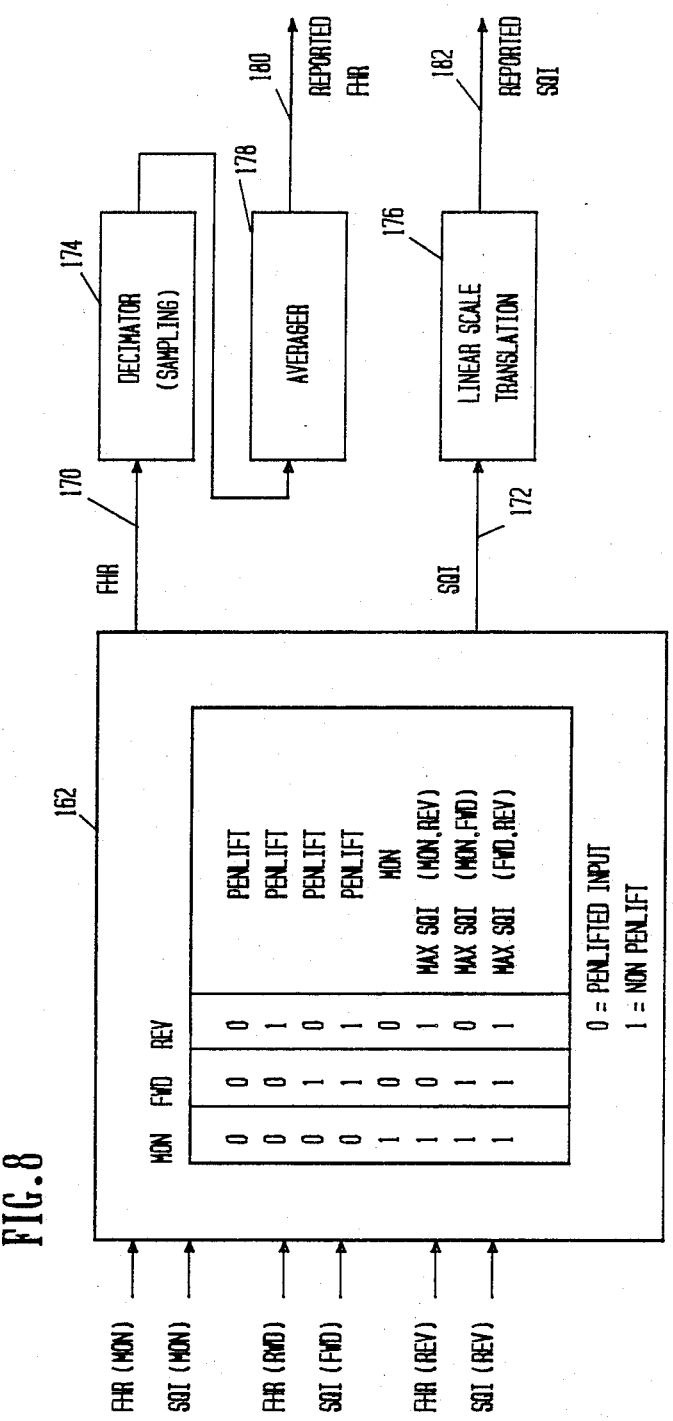
FIG. 8 is a block diagram showing the functional implementation of another part of the FHR counting portion of the system of FIG. 4.

FIG. 8 shows a matrix, i.e. a truth table, of the possible signal combinations for the three modes, FWD, REV and MON. A zero in each place in the table indicates that the FHR count input is a pen lift, while a one indicates an actual FHR count. The routine is organized such that even if the MON FHR count is the only valid (non-penlift) count, the output from 162 is that particular MON FHR count, along with the associated MON SQI index value. The FHR count output appears on FHR line 170 and the SQI index appears on the SQI line 172.

If all three FHR inputs are zero, as shown in the FIG. 8 table, a pen lift signal appears on FHR line 170. If the only valid FHR signal (i.e. a "one") is either FWD or REV, or even both, without a valid MON, a pen lift output flag still occurs on line 170. If either FWD or REV inputs are valid, in addition to the MON input, then the FHR is selected which has the highest, i.e. the best, SQI. If both FWD and REV are valid, in addition to MON, either FWD or REV is selected on the basis of SQI, because the FWD and REV count inputs typically will produce a smoother and more accurate record on the strip chart than the MON input, as long as the signal quality index is a reasonable value. It should be understood, however, that the present invention is not necessarily limited to the particular truth table implementation shown in FIG. 8. For instance, in other implementations, it is not necessary that a valid MON be present in order to have a valid (non-pen-lift) output.

The FHR count from the selected mode will appear on FHR line 170 and its associated SQI value on line 172. The SQI value will always be the SQI value associated with the particular FHR mode selected.

The voted FHR value (i.e. the fetal heart rate data) on line 170 is then applied to a sampling routine 174, while the SQI signal undergoes a linear scale translation at 176. The voted FHR data on line 170 is the composite of successively selected (voted) FHR data for MON, FWD and REV at selected time intervals. The composite FHR data is thus more accurate and more continuous (less pen-lifts) than the FHR data in any single one of the three modes. The FHR data in the embodiment shown is provided at a 10 millisecond rate. This data rate must be matched to the recording/display elements in the fetal monitor. Thus, for a fetal monitor having a 400 millisecond plotting interval, every fortieth (40th) data event on line 170 is sampled by the routine 174. Different sampling rates will be used for different equipment. The sampling function occurs in the j index pointer function referred to above. A five point adaptive averager 178, the function of which is described above with respect to similar averager 160, is used to smooth out the FHR signal. A PLFLAG signal is used to indicate pen-lift.

The SQI signal is also scaled for display on the particular fetal monitor used. The signals on lines 180 and 182 for FHR and SQI, respectively, are applied to the display/printing portion of the fetal monitor for printing on a strip chart. The strip chart is used by a nurse or doctor to monitor the health of the fetus.

Figure 9:
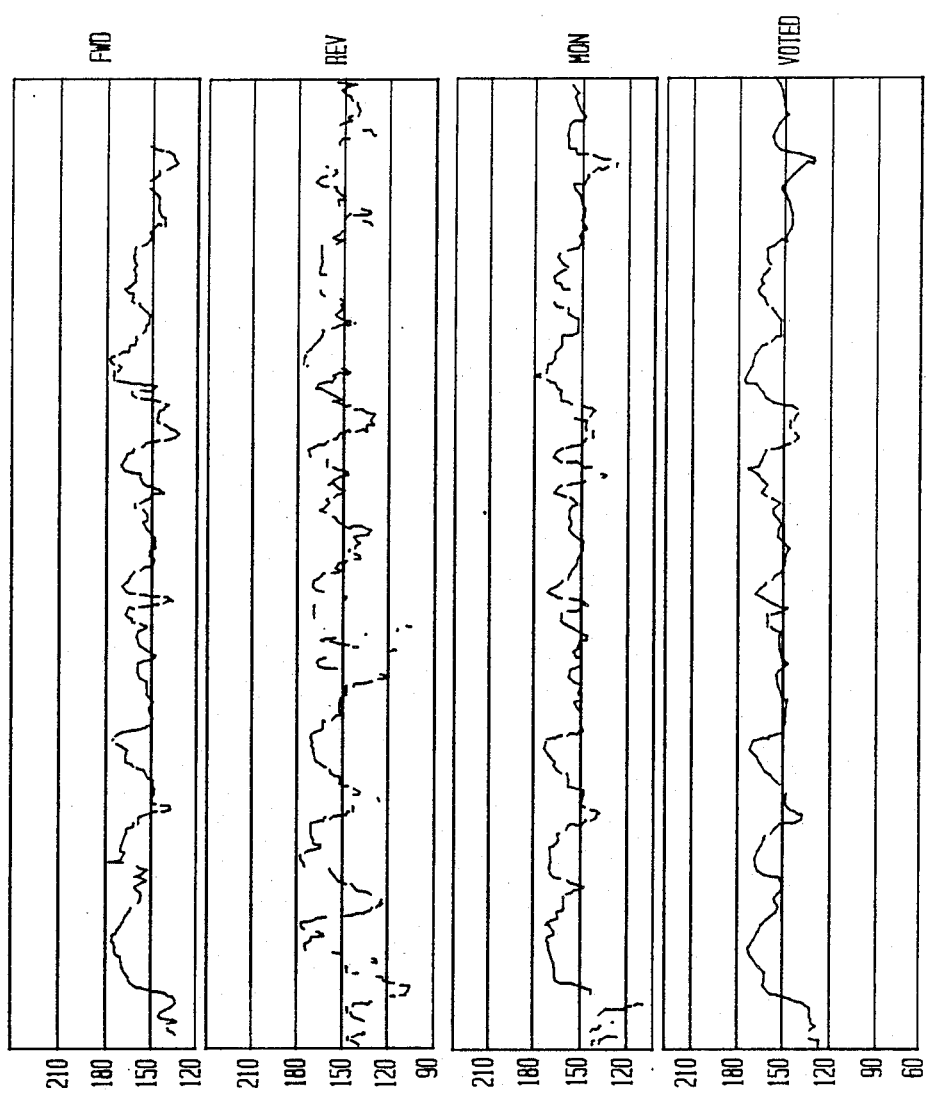
FIG. 9 is a facsimile of a strip chart record showing a fetal heart rate trace produced by the use of the FHR counting system of the present invention.

FIG. 9 shows sample strip charts (FHR traces) for a selected period of time, showing FWD, REV and MON mode FHR data as they might appear as inputs to the voting routine element 162 and the successively selected (voted) FHR data which is reported to the display/printing portion of the fetal monitor. It can be readily seen that the composite FHR trace shown in FIG. 9 is more complete and is a clearer signal, with significantly less interruptions (pen lifts) than any of the other FHR traces, with fewer artifacts (false data). Thus, in the present invention, pen-lifts are minimized, resulting in substantially continuous information concerning fetal heart rate, which is a very desirable result and has been long sought after in the industry.

Thus, a signal processing system has been disclosed which has Doppler signal information provided in a plurality of signal modes. FHR data and SQI information is obtained from the Doppler signal envelope for each mode and then the most accurate FHR data is selected, at successive events, to produce composite FHR data which results in a FHR trace on the strip chart.

Although a preferred embodiment of the invention has been disclosed herein for purposes of illustration, it should be understood that various changes, modifications and substitutions may be incorporated in such embodiment without departing from the spirit of the invention as defined by the claims which follow.

We claim:

1. A system for determining fetal heart rate data for use in a fetal monitor, comprising:
   means for transmitting a signal into the fetal heart while the fetus is in utero;
   means for receiving a returning Doppler signal from the fetus, frequency-shifted by action of the fetal heart;
   means for processing the returning Doppler signal so as to produce simultaneously a plurality of processed Doppler signals occupying a common band of frequencies, each processed Doppler signal representing a different component of the returning Doppler signal and containing fetal heart rate data;
   means for obtaining fetal heart rate data from each of said processed Doppler signals; and
   means for selectively combining the fetal heart rate data obtained from said processed Doppler signals in such a manner as to produce composite fetal heart rate data which is more accurate than the fetal heart rate data obtained from any of the processed Doppler signals individually.

2. The system of claim 1, wherein said means for processing the returning Doppler signal includes means operating on said returning Doppler signal to produce a direct Doppler signal and a quadrature Doppler signal, said returning Doppler signal processing means further including demodulator means operating on said direct and quadrature Doppler signals to produce first, second and third demodulated Doppler signals, wherein the first demodulated Doppler signal is obtained by adding the quadrature Doppler signal to the direct Doppler signal and demodulating the result, wherein the second Doppler signal from the quadrature Doppler signal and demodulating the result, and wherein the third demodulated Doppler signal is obtained by demodulating the direct Doppler signal.

3. A system of claim 2, wherein said means for operating on said returning Doppler signal includes a signal mixer for mixing the transmitted signal with the returning Doppler signal to produce the direct Doppler signal, and a second signal mixer for mixing the returning Doppler signal with a 90° phase shifted transmitted signal to produce said quadrature Doppler signal.

4. A system of claim 1, wherein said means for transmitting and said means for receiving comprises a single transducer means having transmitting and receiving elements, the transducer being adapted for positioning on the abdomen of the mother.

5. A system of claim 1, including first and second microprocessors and a memory element shared non-simultaneously by said first and second microprocessors, wherein in operation the first microprocessor obtains a selected amount of direct Doppler signal information and quadrature Doppler signal information and stores said direct and quadrature signals in said memory, and wherein the second microprocessor means processes said direct and quadrature signals, by means of software, in said second microprocessor means, to produce said composite fetal heart rate data, and wherein said first microprocessor means includes means communicating with a portion of the fetal monitor for display of said composite fetal heart rate data in the form of a fetal heart rate trace.

6. A system of claim 1, including means for producing an indication of signal quality for the composite fetal heart rate data.

7. A system for determining optimum fetal heart rate data from a plurality thereof, comprising:
   means for obtaining a plurality of fetal heart rate data from a single returning Doppler signal, wherein each of the plurality of fetal heart rate data is the result of a different signal processing of the returning Doppler signal and thereby represents a different component of the returning Doppler signal;
   means for determining at successive points in time the validity of each of said plurality of fetal heart rate data;
   means for determining the signal quality of each fetal heart rate data at said successive points in time; and
   means selecting a valid one of said plurality of fetal heart rate data in accordance with preselected criteria at said successive points in time, including the signal quality of the valid fetal heart rate data.

8. A system of claim 7, wherein said selecting means includes means selecting none of the valid fetal heart rate data under selected conditions.

9. A system of claim 8, wherein said selecting means includes means selecting none of the plurality of fetal heart rate data if a pre-selected one thereof is not valid and means selecting the one fetal heart rate data having the best signal quality from among the valid fetal heart rate data having a valid heart rate at those selected points in time where said pre-selected one data is valid.

10. A system of claim 9, wherein the selected fetal heart rate data than said pre-selected fetal heart rate data in the event that all the fetal heart rate data are valid at said one point in time.

11. A system of claim 9, wherein one fetal heart rate data is representative of the forward movement of the fetal heart valve, wherein a second fetal heart rate data is representative of the reverse movement of the fetal heart valve, and wherein the pre-selected one of said fetal heart rate data is representative of the entire returning Doppler signal.

12. A system of claim 7, wherein said system includes means for providing the selected fetal heart rate data on one output line and a valve indicative of signal quality for the selected fetal heart rate data on another output line.

13. A system of claim 7, including means for sampling the selected fetal heart rate data on the one output line so as to match the selected fetal heart rate data to a display portion of a selected fetal monitor.

14. A system for quadrature demodulation of a returning fetal heart rate Doppler signal which has been initially processed to produce a first Doppler signal and a second Doppler signal in quadrature relative to the first signal, comprising:

means for adding the second Doppler signal to the first Doppler signal, producing a first processed Doppler signal;
means for subtracting the first Doppler signal from the second Doppler signal, producing a second processed Doppler signal;
means for providing the first Doppler signal unprocessed; and
means rectifying the first processed Doppler signal to produce a first demodulated Doppler signal, rectifying the second processed Doppler signal to produce a second demodulated Doppler signal and rectifying the unprocessed first Doppler signal to produce a third demodulated Doppler signal, wherein the first demodulated Doppler signal represents fetal heart rate information corresponding to forward movement of the fetal heart valve and wherein said second demodulated Doppler signal represents fetal heart rate information corresponding to reverse movement of the fetal heart valve.

15. A system of claim 14, including means for low-pass filtering the first, second and third demodulated Doppler signals and for sampling the first, second and third demodulated Doppler signals at a selected rate.

16. A system for determining fetal heart rate from a demodulated Doppler signal returning from a fetus in utero, comprising:
   means for making a logarithmic compression of the demodulated Doppler signal;
   means for differentiating the log-compressed Doppler signal;
   means for detecting the zero crossings of the differentiated Doppler signal, wherein the zero crossings are indicative of a fetal heart beat;
   means for determining the number of fetal heart beats in a selected period of time from said zerocrossings to produce fetal heart rate data from said demodulated Doppler signal.

17. A system of claim 16, wherein said determining means includes means for calculating the edges of the zero crossings, means for calculating the number of fetal heart beats from the number of trailing edges of the zero crossings and means for averaging the two calculations.

18. A system of claim 16, including means for low-pass filtering the demodulated Doppler signal so as to limit the Doppler signal to frequencies in the range of normal fetal heart rates.

19. A system of claim 18, including means for squelching the demodulated Doppler signal, with a threshold of approximately 0.002000.

20. A system of claim 16, including means for interpolating the number of fetal heart beats between successive actual detected heart beat events.

21. A system of claim 16, wherein the fetal heart rate data is displayed on a strip chart in the form of a fetal heart rate trace and wherein said system includes means for determining non-valid fetal heart rate data and preventing display of said non-valid fetal heart rate data.

22. A system for determining signal quality for a demodulated Doppler signal, comprising:
   means for determining fetal heart rate data from the demodulated Doppler signal;
   means for determining a signal to noise ratio estimate of the demodulated Doppler signal;
   means determining whether or not the signal to noise ratio estimate is above a pre-selected level, and for eliminating fetal heart rate data when the signal to noise ratio estimate is below said selected level thereby producing valid fetal heart rate data;

means calculating the time between successive fetal heart beats in the valid fetal heart rate data; and means obtaining the average time difference value between successive fetal heart beats in the valid fetal heart rate data, said average time difference value being an indication of signal quality of the demodulated Doppler signal.

23. A system of claim 22, including means for squelching the demodulated Doppler signal prior to the determination of the signal to noise ratio estimate, the threshold level of the squelch being approximately 0.002000.

24. A system of claim 22, including means for filtering the output of the calculating means.

25. A system of claim 22, wherein the time difference averaging means is a 7 point adaptive averager.

* * * * *

UNITED STATES PATENT AND TRADEMARK OFFICE
CERTIFICATE OF CORRECTION

PATENT NO. : 4,890,624

DATED : Jan. 2, 1990

INVENTOR(S) : Dipankar Ganguly, Gary B. Sanders

It is certified that error appears in the above—identified patent and that said Letters Patent is hereby corrected as shown below:

Column 3, line 18 change "90√" to --90°--.

Column 4, line 7 change "microprocessor 39" to --microprocessor 38--.

Column 5, line 9 change "deoimated" to --decimated--.

Reformat column 9 lines 56-68 and column 10 lines 1-4 as follows:

```
--if       EVENT(n) > Item(1)

then     Item(3)' = Item(2)
           Item(2)' = Item(1)    MEDF(n) = Item(1)
           Item(1)' = EVENT(n)

if       Item(2) < EVENT(n) < Item(1)

then     Item(3)' = Item(2)
           Item(2)' = EVENT(n)   MEDF(n) = EVENT(n)
           Item(1)' = Item(1)

if       Item(3) < EVENT(n) < Item(2)

then     Item(3)' = EVENT(n)
           Item(2)' = Item(2)    MEDF(n) = Item(2)
           Item(1)' = Item(1)

if       EVENT(n) < Item(2)

then     Item(3)' = EVENT(n)
           Item(2)' = Item(3)    MEDF(n) = Item(3)
           Item(1)' = Item(2)--.
```

UNITED STATES PATENT AND TRADEMARK OFFICE
CERTIFICATE OF CORRECTION

PATENT NO. : 4,890,624            Page 2 of 2
DATED : Jan. 2, 1990
INVENTOR(S) : Dipankar Ganguly, Gary B. Sanders It is certified that error appears in the above—identified patent and that said Letters Patent is hereby corrected as shown below:

Column 11 line 37 change "BEAT(N)" TO --BEAT(n)--.

Column 11 lines 47 through 49 change
    "BEAT(n) = input data processed in step (a)" to
    --BEAT(n) = output of averager
      BPM'(n) = input data processed in step (a)--.

Column 14 line 50 after "Doppler signal" insert -- is obtained by subtracting the direct Doppler signal --.

Column 15 line 44 after "heart rate data" insert -- at any one point in time is other --.

Column 15 line 57 change "valve" to --value--.

Column 16 line 35 change "zerocrossings" to --zero-crossings--.

Signed and Sealed this

Twenty-ninth Day of January, 1991

Attest:

HARRY F. MANBECK, JR.

*Attesting Officer*      *Commissioner of Patents and Trademarks*